US005564262A

United States Patent [19]
Bevis et al.

[11] Patent Number: 5,564,262
[45] Date of Patent: Oct. 15, 1996

[54] LIGACLIP LOADING MACHINE AND PROCESS

[75] Inventors: Brian Bevis, Saugus, Calif.; Bela Vincze, Flemington, N.J.; Alan Deeter, Santa Cruz, Calif.

[73] Assignee: Ethicon, Inc., Somerville, N.J.

[21] Appl. No.: 504,300

[22] Filed: Jul. 20, 1995

[51] Int. Cl.⁶ .............................. B65B 5/08; B65B 35/14
[52] U.S. Cl. ................................ 53/471; 53/246; 53/250; 53/253; 53/475
[58] Field of Search .............................. 53/473, 474, 475, 53/471, 467, 485, 253, 249, 250, 251, 246, 244, 255, 282, 235

[56] References Cited

U.S. PATENT DOCUMENTS

| | | | |
|---|---|---|---|
| 3,054,237 | 9/1962 | Barkstrom | 53/246 |
| 4,048,781 | 9/1977 | Johansen | 53/471 X |
| 4,201,027 | 5/1980 | Ilsemann | 53/253 X |
| 4,835,939 | 6/1989 | Thomas et al. | 53/253 X |
| 5,207,050 | 5/1993 | Fulkerson et al. | 53/474 |
| 5,285,620 | 2/1994 | Kaye et al. | 53/474 |

*Primary Examiner*—James F. Coan
*Attorney, Agent, or Firm*—Emil Richard Skula

[57] ABSTRACT

An apparatus for loading ligating clips into ligating clip cartridges. The apparatus has a frame and a rotatable indexing table mounted to the frame. A plurality of nest members for holding cartridges and cartridge components is mounted to the outer periphery of the indexing table. The nest are rotated and indexed to a plurality of work stations located proximately on or about the frame. Components are loaded into the nest members at the work stations to form assembled cartridges loaded with ligating clips. One work station removes the assembled cartridges from the nest members.

19 Claims, 12 Drawing Sheets

LIGACLIP LOADING MACHINE AND PROCESS

TECHNICAL FIELD

The technical field to which this invention relates is surgical ligating clips, in particular machinery and a process for loading surgical ligating clips into clip cartridges.

BACKGROUND OF THE INVENTION

Surgical ligating clips are well known in the surgical arts. The surgical ligating clips are used in surgical procedures to clip and secure various types of blood vessels. The clips are applied with conventional clip appliers. In such clip appliers, a clip is maintained between a pair of jaws which are actuated to cause the clip to be formed about a blood vessel. Conventional clip appliers can be classified as single clip appliers wherein a clip must be manually loaded into the jaws from a separate clip holding cartridge prior to each use, or multiple clip appliers wherein a clip is automatically or semiautomatically loaded into the jaws from an integral magazine prior to each use.

In order to facilitate the use of a single clip applier, manufacturers have typically packaged ligating clips in cartridges which facilitate the loading of the clips into the jaws of a clip applier. A cartridge will typically consists of a base and a cover. A plurality of clips, e.g., six, is typically contained in the cartridge in separated cavities. A clip is loaded from the cartridge into the jaws of the clip applier by inserting the jaws into an opening contained within the cover and into an underlying cavity containing a clip. A ligating clip is then typically secured within the jaws by interlocking mechanical engagement projections on the clip and the inner surfaces of the jaws.

Ligating clip cartridges have been conventionally loaded by hand. Each ligating clip is manually loaded into an individual cavity within the cartridge. It can be appreciated that manually loading a cartridge with ligating clips is a costly, tedious and time consuming procedure. In addition, the nature of such a procedure can result in inadvertent operator error wherein the operator fails to insert a clip in each cavity of the cartridge. Therefore, what is needed in this art is an apparatus to automatically load ligating clips into ligating clip cartridges.

SUMMARY OF THE INVENTION

It is an object of the present invention to provide an apparatus and method for automatically loading ligating clips into a ligating clip cartridge.

Accordingly an apparatus for automatically loading a plurality of ligating clips into a ligating clip cartridge, wherein the cartridge comprises a base and a cover having a plurality of cavities for receiving ligating clips, is disclosed. The cartridge cover has openings in the cover in communication with the cavities. The cartridge base fits into the cartridge cover. The apparatus has a base member having a top. An index table member is rotatably mounted to the top of the base member. The index table member has a top, a bottom and an outer periphery. An indexing motor and transmission rotate the index table member. The motor is mounted to the base member. At least one nest member is mounted to the periphery of the index table member. Each nest member has a cavity for receiving a ligating clip cover and base member. A follower means is mounted to each nest member for raising and lowering the nest member with respect to the index table member. Cam means are mounted to the base adjacent to each work station for engaging the cam follower means. A first work station is located proximately to the index table. The first work station has a base. The first work station has a pick and place unit mounted to a base which places a cover in the cavity of each nest member. A second work station is located on the top surface of the base member proximate to the index table, said second work station has a slider plate for feeding at least one ligating clip into cavities contained in a clip cover mounted in the cavity of a nest member. The nest member can be indexed with respect to the slider plate so that a ligating clip can be inserted in each cavity of the cover. A third work station is also located proximate to the index table. The third work station has a pick and place apparatus for inserting a base into a clip cover containing at least one ligating clip mounted in the cavity, thereby completing the assembly of the ligating clip cartridge. A fourth work station is located proximate to the index table on the top of the base member. The fourth work station has a pick and place unit for removing an assembled ligating clip cartridge from the cavity of each nest member. The apparatus has an indexing assembly for indexing the index table member so that each nest member is successively moved to each work station. Optionally, one or more optical inspection work stations are located proximate to the indexing table for inspection of the cavities of the nests at various positions between the work stations.

Yet another aspect of the present invention is a method of loading ligating clip cartridges with ligating clips using the above-described apparatus.

The foregoing and other features and advantages of the present invention will become more apparent from the following description and accompanying drawings.

BEST MODE FOR CARRYING OUT THE INVENTION

The disclosure of commonly owned U.S. patent application Ser. No. 08/277,848 filed on Jul. 20, 1994 is incorporated by reference.

An apparatus 10 of the present invention is illustrated in FIGS. 1 and 5–15. The apparatus 10 is utilized to load ligating clips 2 into a ligating clip cartridge 690. The apparatus 10 also assembles the cartridge 690.

Figure 2:
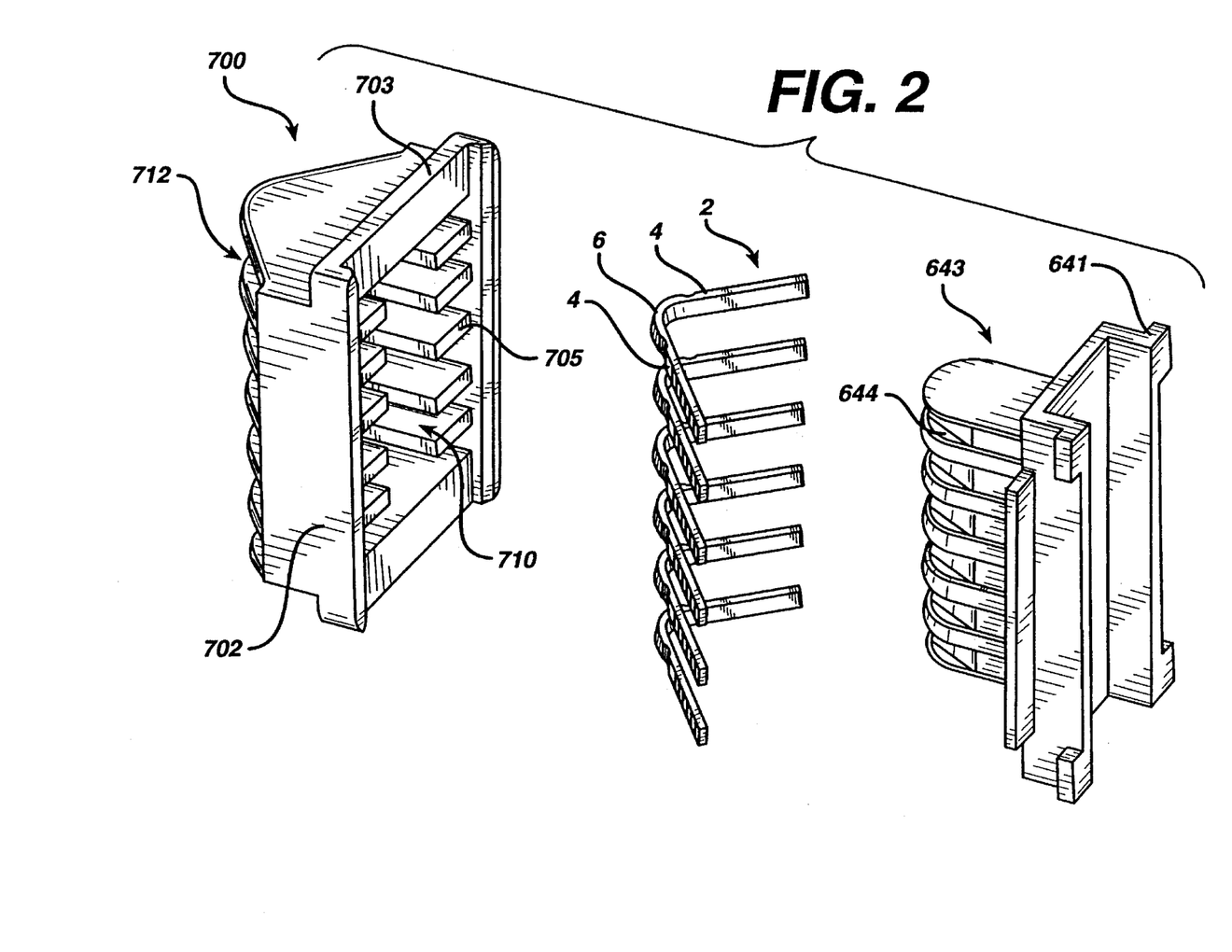
FIG. 2 is an exploded perspective view of a ligating clip cartridge and ligating clips loaded by the apparatus of the present invention.
Figure 3:
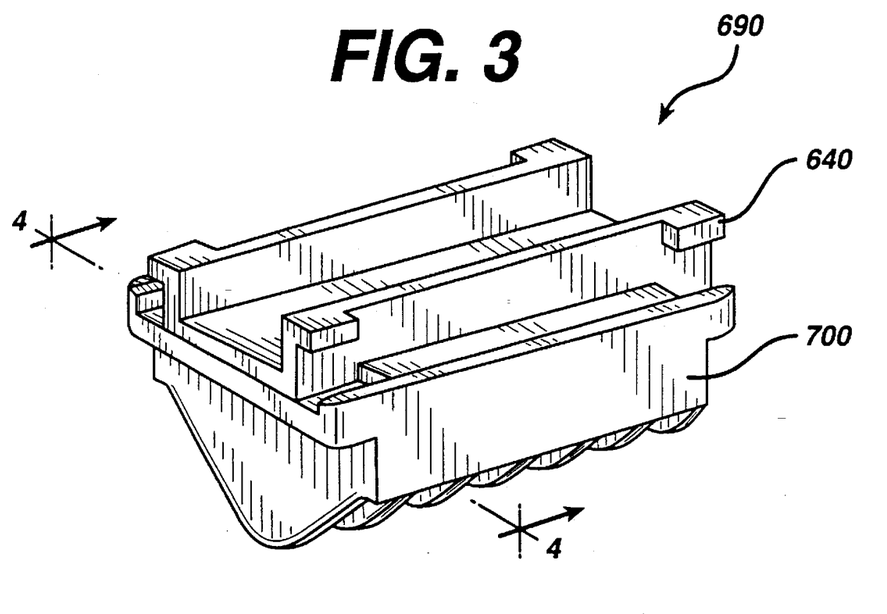
FIG. 3 is a perspective view of a loaded ligating clip cartridge.
Figure 4:
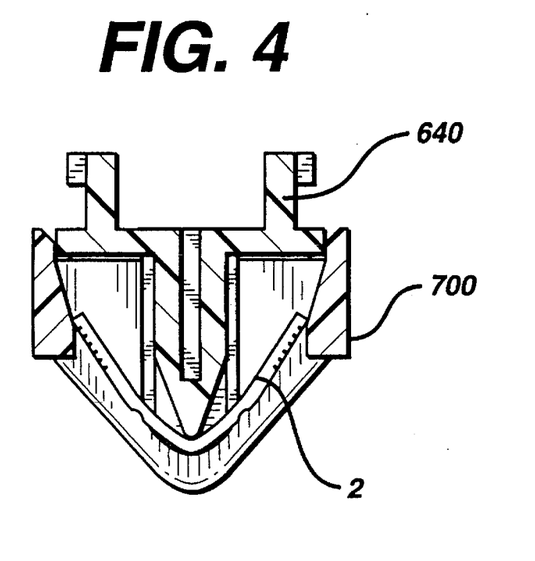
FIG. 4 is a cutaway view of the ligating clip cartridge of FIG. 3 taken along View Line 4—4.

Referring to FIGS. 2–4, the cartridge 690 is seen to consist of a base 640 and a cover 700. The cover 700 is seen to have a plurality of cavities 710 for receiving ligating clips 2. Access holes 712 through the top of cover 700 are seen to be in communication with each cavity 710. Ligating clip cartridges are known in the art, e.g., U.S. Pat. No. 3,713,533 which is incorporated by reference. Ligating cartridges typically will have a plurality of cavities for receiving the ligating clips and access holes in communication with the cavities through which the jaws of a ligating clip applier are inserted to load ligating clips.

Referring to FIG. 2, the ligating clips 2 which are packaged in cartridges using the apparatus of the present invention are seen to be conventional ligating clips having a pair of legs 4 joined at an apex 6. The legs 4 are angulated with respect to each other. The cartridge 690, as previously described, is seen to consist of a cartridge base 640 and a cartridge cover 700.

The cartridge cover 700 is seen to have a pair of opposed triangularly shaped end pieces 704. The cover 700 is also seen to have a substantially rectangular frame having a pair of opposed major sides 702 connected by a pair of opposed minor sides 703. A plurality of rib members 705 extending from the interior of the major sides 702 form cavities 710 for receiving ligating clips 2. Openings 712 at the top of each cavity 710 are in communication with the cavities 710.

The cartridge base 640 is seen to have a rectangular frame 641. Extending from the top of the rectangular frame 641 is the member 643. The member 643 has grooves 644 corresponding to the cavities 710 such that when the cartridge 690 is assembled by inserting the base 640 into the cover 700, the ligating clips 2 are each contained with the cavities 710 and the grooves 644.

Figure 1:
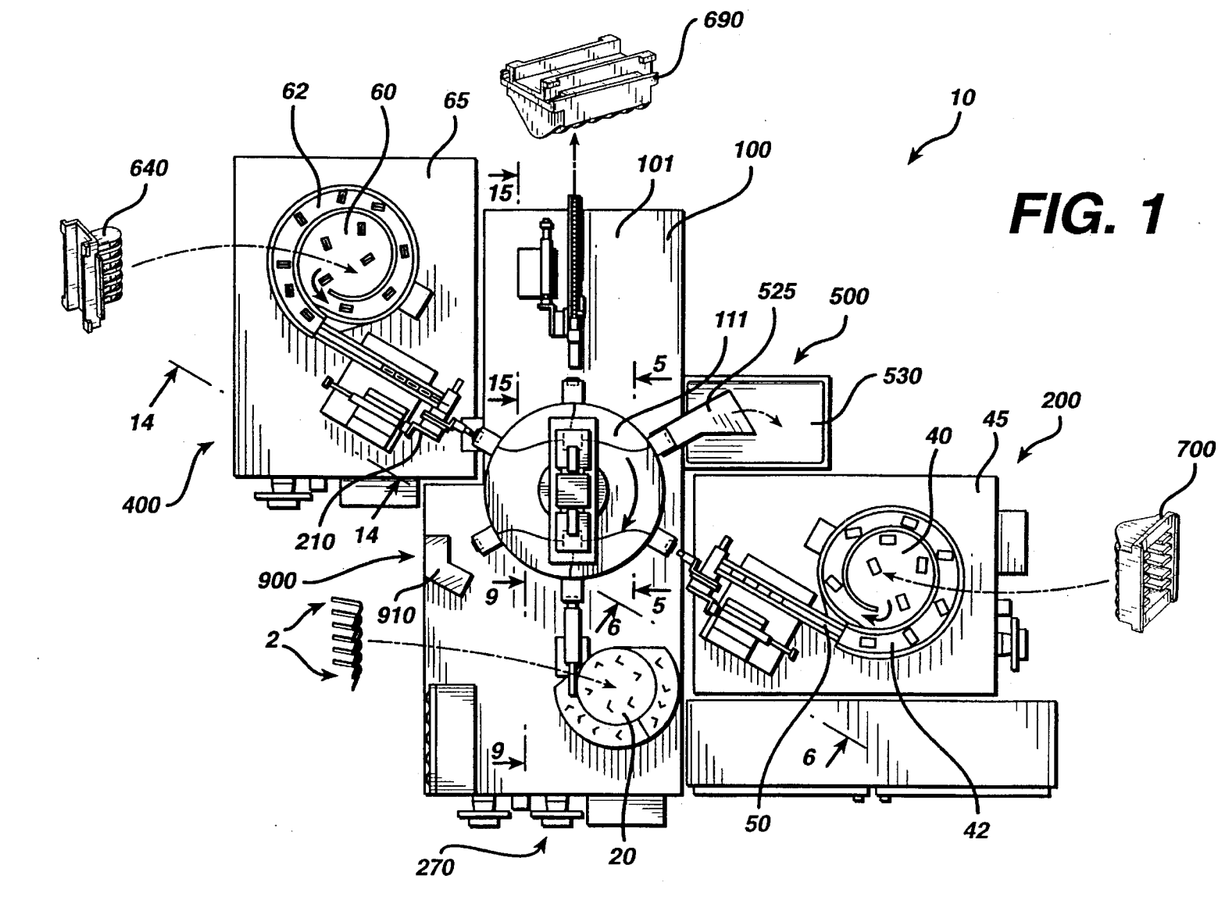
FIG. 1 is a top view of the apparatus of the present invention.

The apparatus 10 of the present invention as illustrated in FIG. 1 is seen to consist of a first vibratory bowl 20 connected to a track 30 mounted to the top 101 of frame 100. Vibratory bowl 20 contains ligating clips 2. Vibratory bowl 20 is a conventional vibratory bowl feed apparatus wherein controlled vibration of the bowl 20 causes clips to translate along the spiral ramp 22 to the conventional track 30. Track 30 is also vibrated to move the ligating clips 2 to a clip feeding mechanism described hereinbelow. The apparatus 10 also has a second conventional vibrating bowl 40 to feed covers 700 along a spiral ramp 42 to a conventional track 50. Bowl 40 is mounted to base 45. A third conventional vibrating bowl 60 feeds bases 640 along a spiral ramp 62 to a conventional track 70. Bowl 60 is mounted to base 65. Tracks 50 and 70 are also vibrated.

Figure 5:
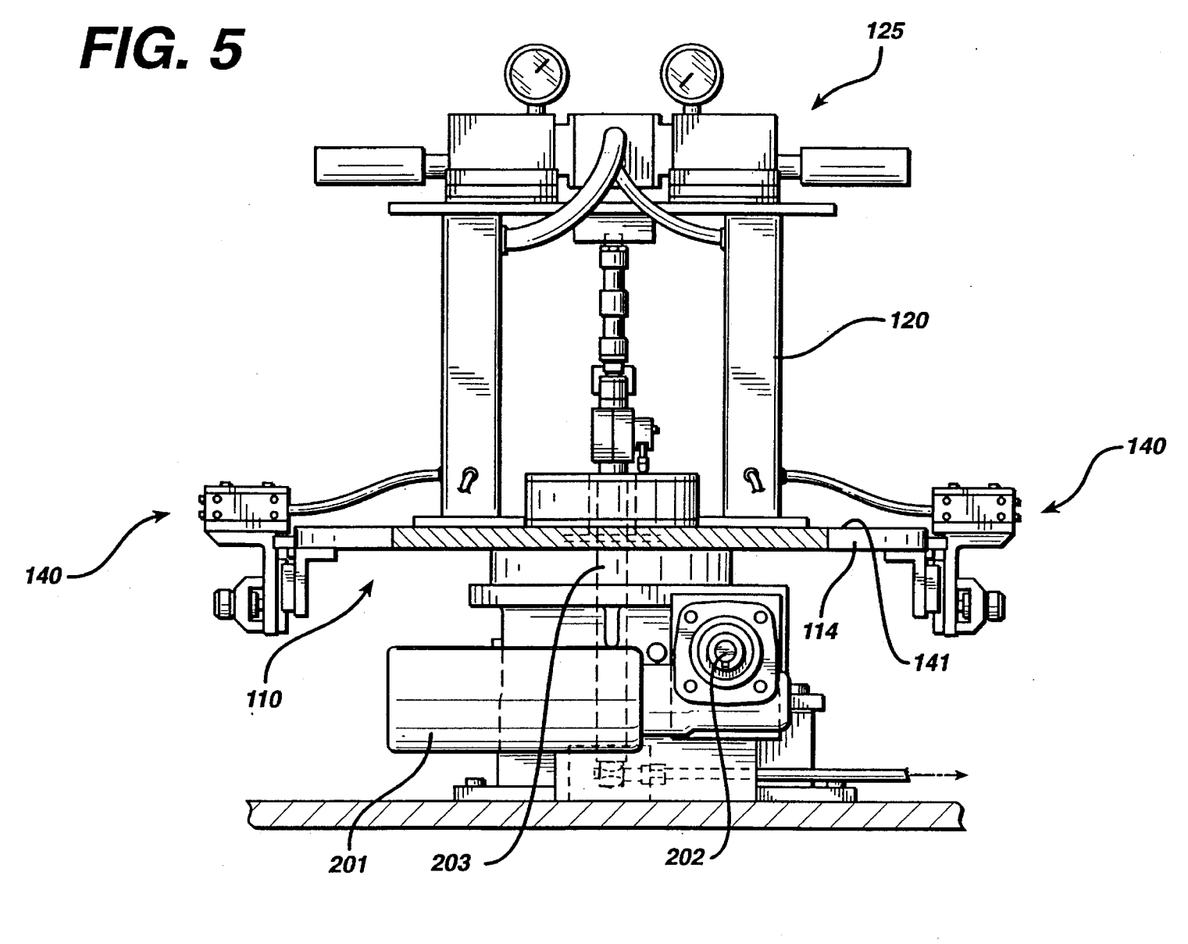
FIG. 5 is a front view of the apparatus of FIG. 1.
Figure 6:
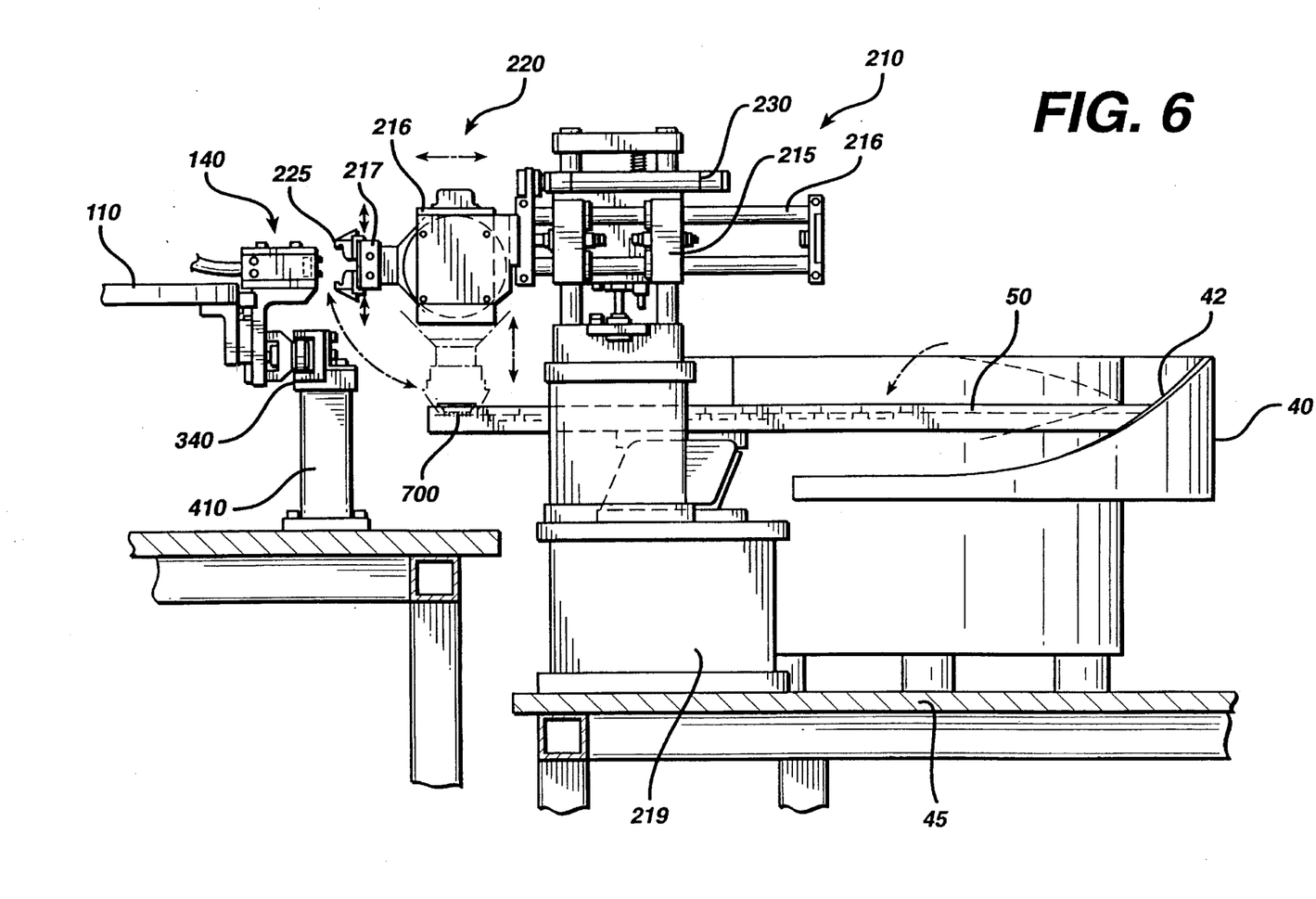
FIG. 6 is a side view of the apparatus of FIG. 1.
Figure 7:
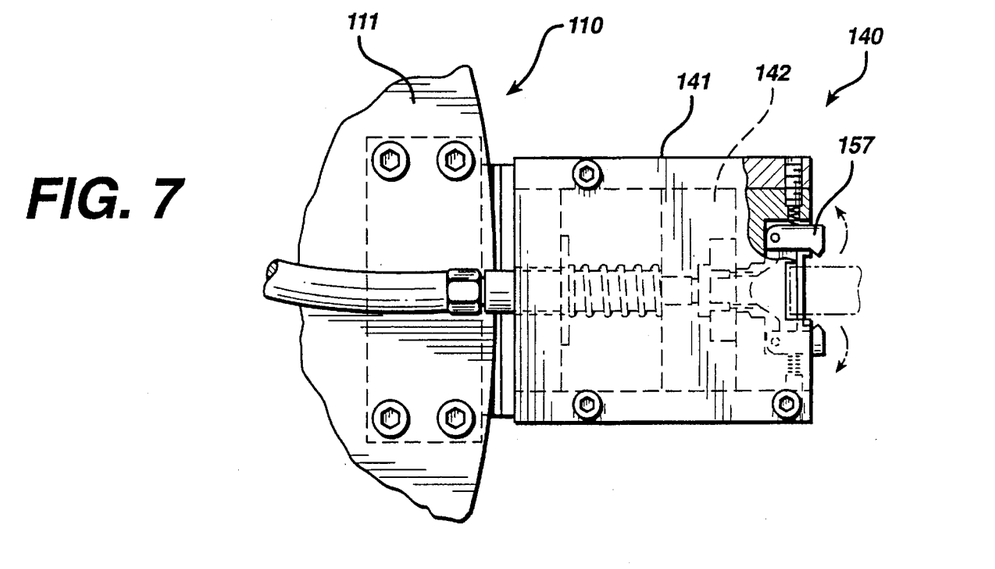
FIG. 7 is a partial top view illustrating a nest element.
Figure 8:
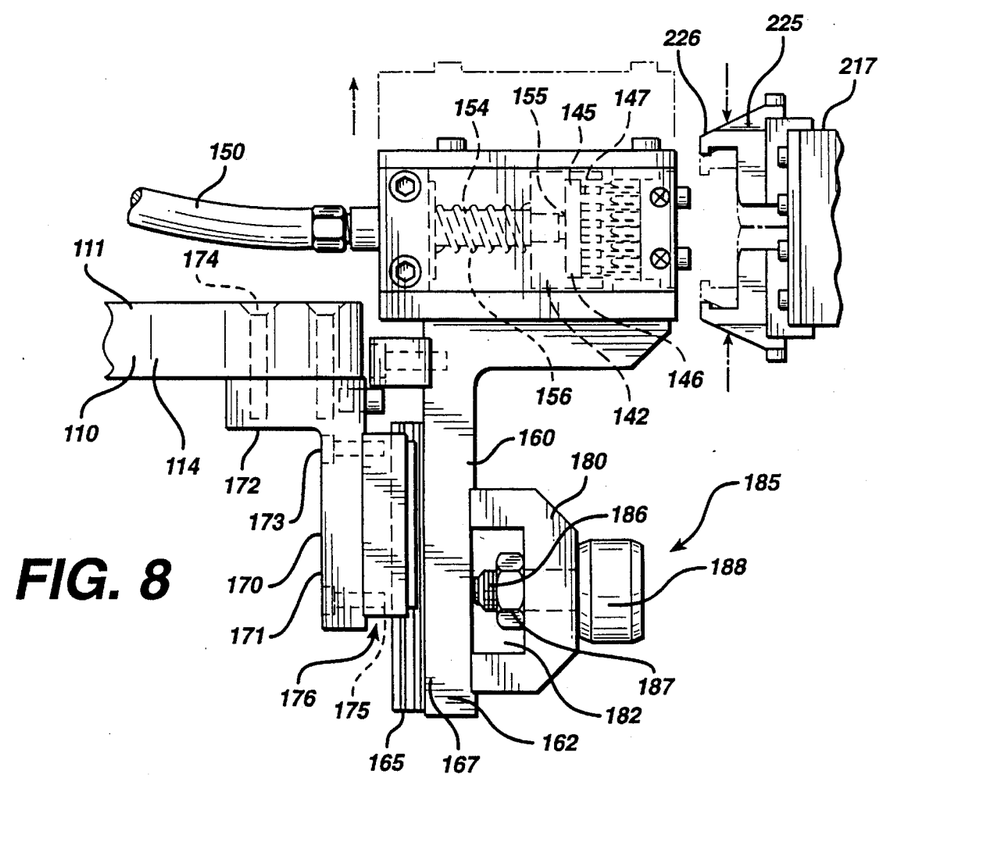
FIG. 8 is a partial side view illustrating a nest element containing an assembled cartridge.
Figure 9:
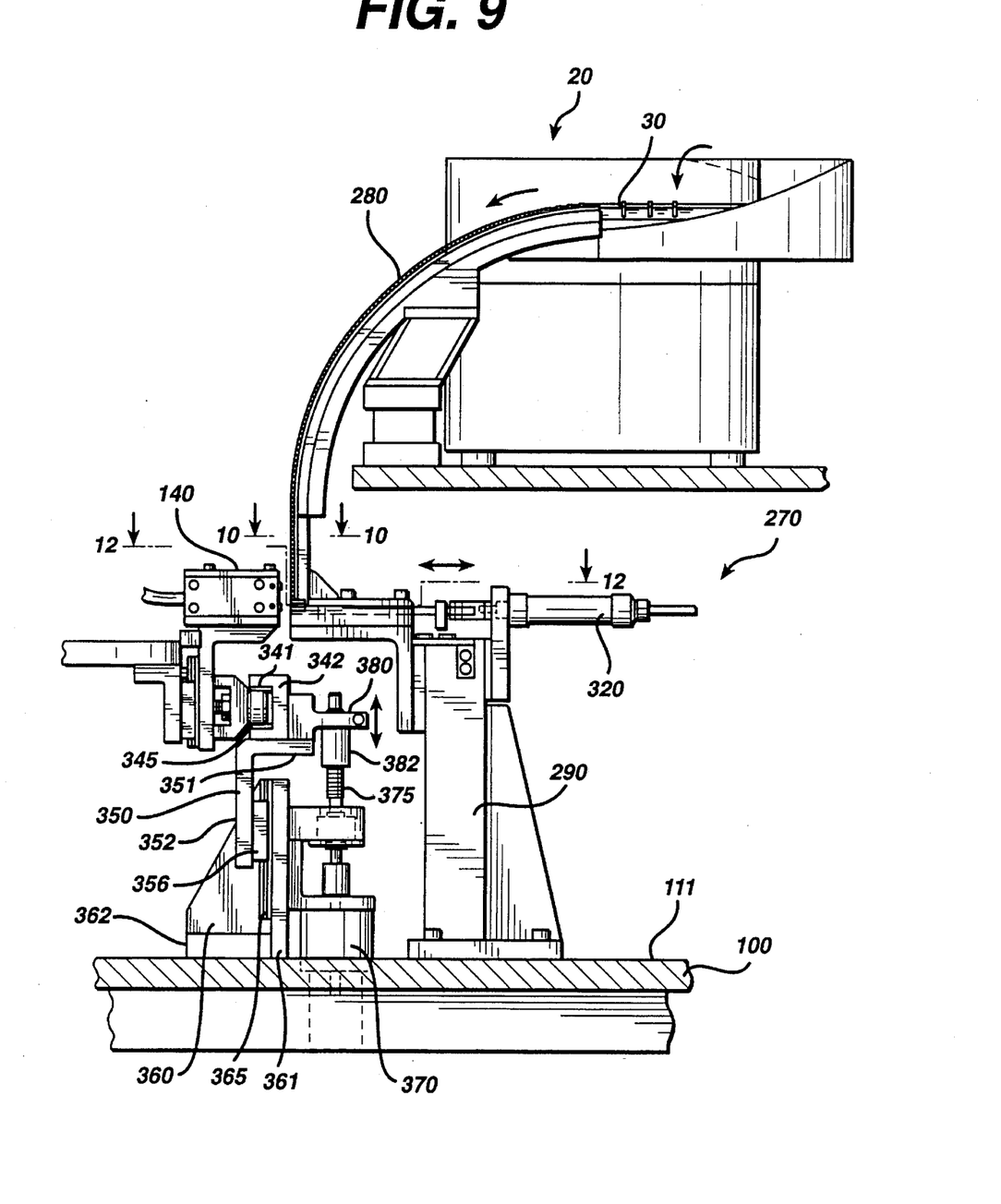
FIG. 9 is a partial side view illustrating the ligating clip feeding bowl and rail.
Figure 10:
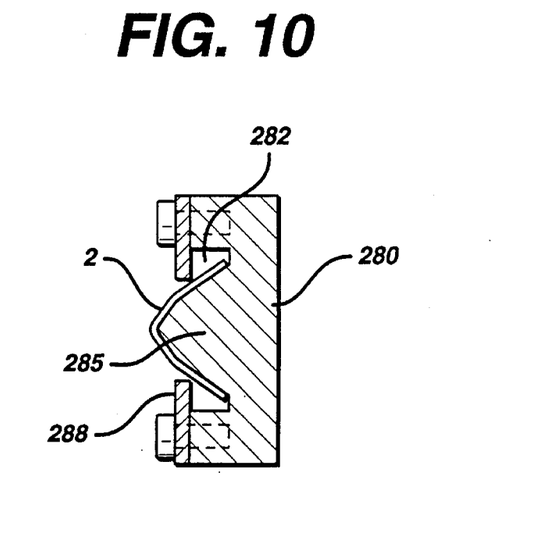
FIG. 10 is a cross-sectional view of the apparatus of FIG. 9 illustrating a ligating clip positioned on the feed rail taken View Line 10—10.
Figure 11:
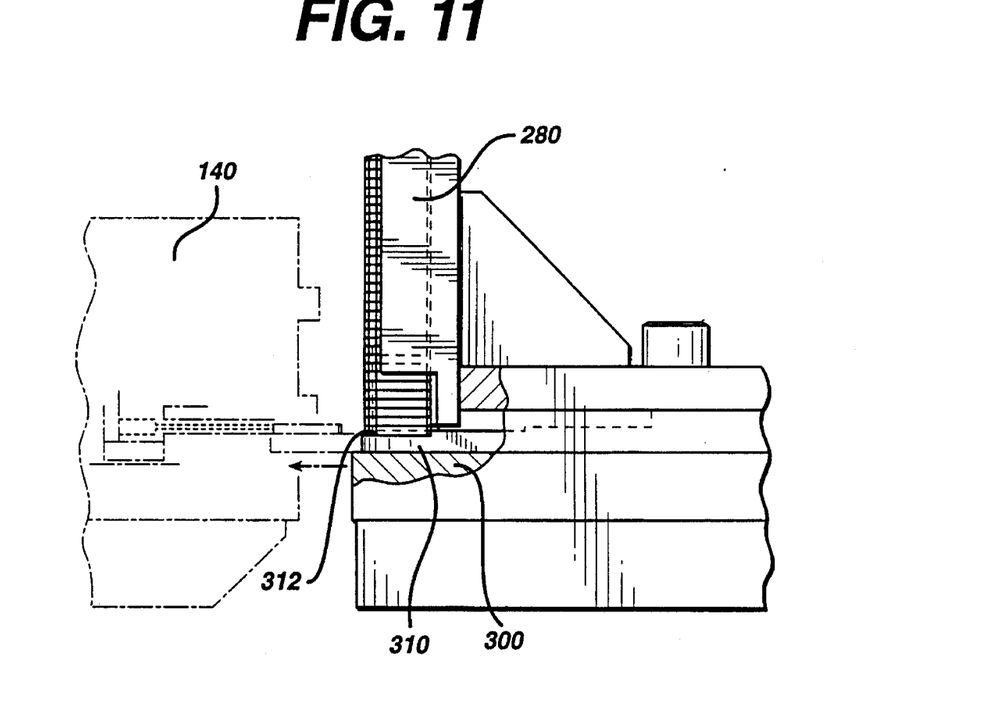
FIG. 11 is a partial side view illustrating the clip feeding mechanism.
Figure 12:
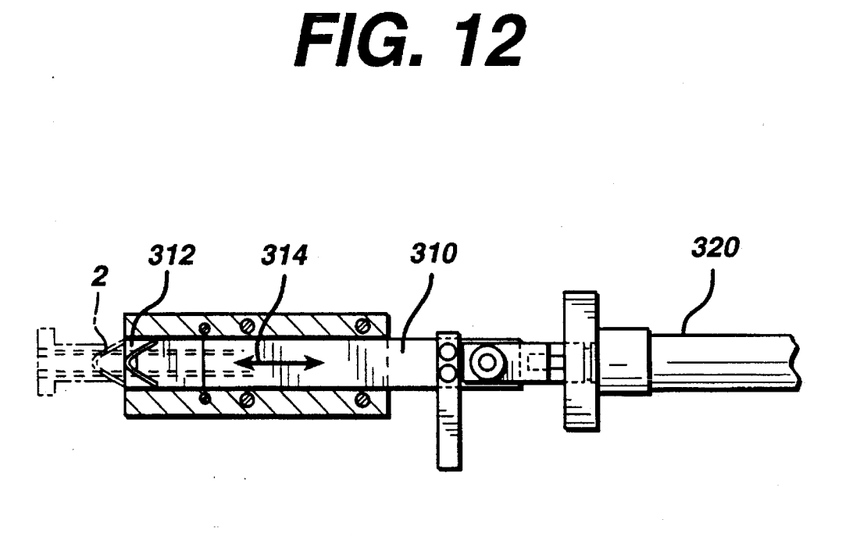
FIG. 12 is a partial cross section view taken along View Line 12—12 of the apparatus of FIG. 9.
Figure 13:
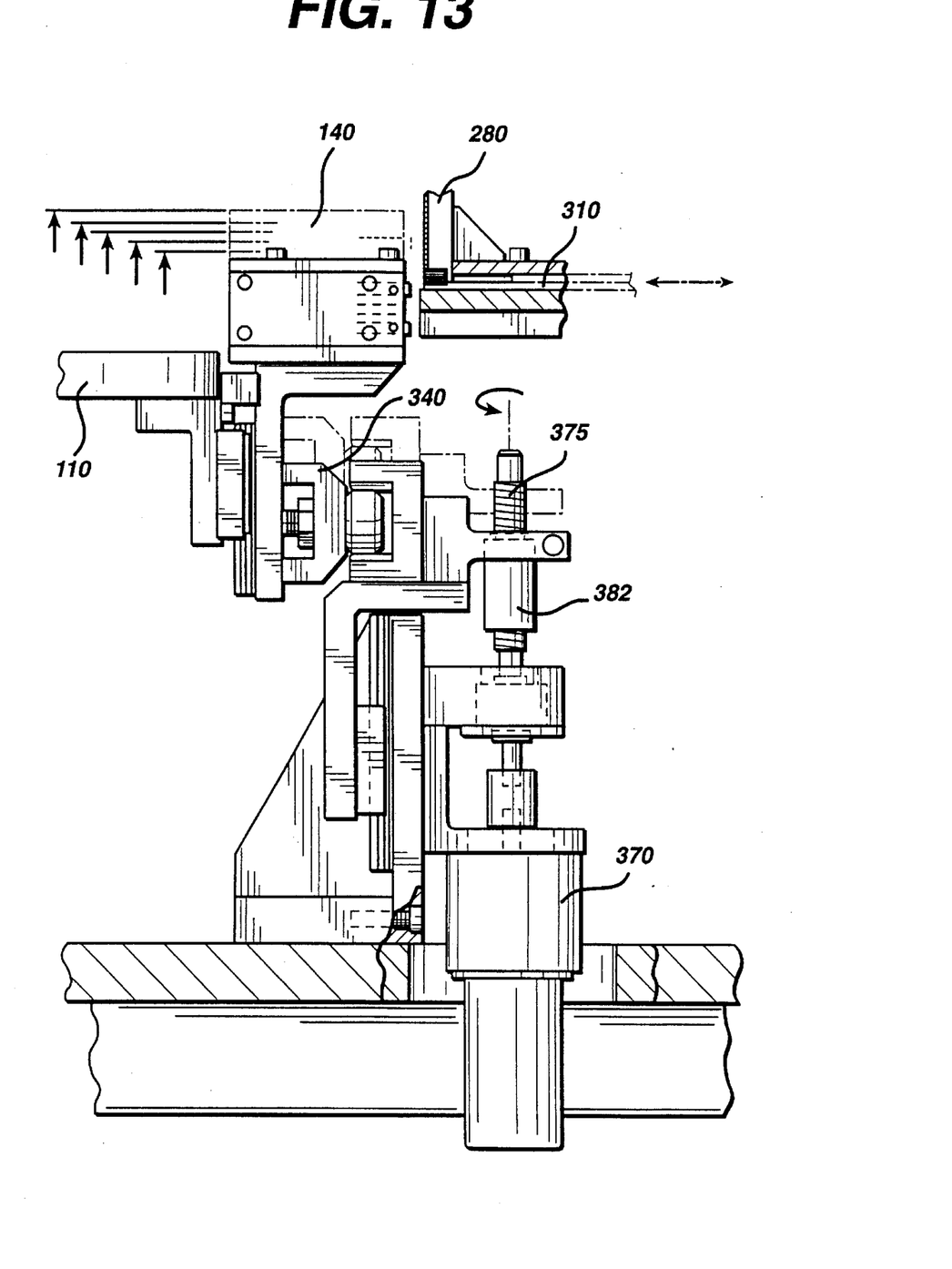
FIG. 13 is a partial side view of the apparatus of the present invention illustrating the vertical movement of a nest as ligating clips are loaded into the cartridge.

Referring now to FIG. 1 and FIGS. 5–15, the apparatus 10 is seen to have frame 100. Rotary index table 110 is seen to be rotatably mounted to the top 101 of the frame 100. The rotary index table 110 is seen to be a circular disk-like member having topside 111 having periphery 112. Side 114 is seen to extend downwardly from top 111 around periphery 112. Mounted about the periphery 112 of the rotary index table 110 are the nest members 140. Six nest members 140 are illustrated in FIG. 1, however any number of nest members can be utilized. The nest members 140 are preferably equidistantly spaced about the periphery of table 110. As illustrated in FIGS. 7 and 8, the nest members 140 are seen to have frames 141 having internal plenum cavities 142 and openings 143 for receiving covers 700 and bases 640. Mounted in the cavity 142 of each nest member 140 are the comb members 145 having frames 146 teeth 147. Shaft 148 extends from the back side of frame 146. Vacuum hose 150 is seen to be mounted to vacuum port 151 using a conventional connector. Vacuum port 151 extends through frame 141 and connects with cavity 142. Support tube 154 is seen to extend from the inner closed end of frame 141. Spring member 156 is seen to be mounted concentrically about tube 154 and provides a biasing force against comb member 145. The shaft 148 is seen to be slidably mounted in tube 154. The nest members 140 are seen to have pivotally mounted, spring biased jaws 157 mounted near opening 143 in frame 141. Springs 158 are mounted in frame 141 and bias jaw members 157. Jaw members 157 open and close as cartridge components and cartridges are inserted and/or removed from nests 140. The frame 141 of nest member 140 is mounted to support bracket 160, which is in turn slidably mounted to retention plate 175, which is in turn mounted to lower leg 171 of mounting bracket 170 by mounting screws 173. The upper leg of 172 of mounting bracket 170 is mounted to the bottom of index table 110 by the machine screws 174. Mounted to the downward leg 102 of mounting bracket 160 is the cam support bracket 180. Cam support bracket 180 is seen to have passage 182 for receiving the shaft 186 of roller cam 185. Roller cam 185 is secured to bracket 180 by the nut 187. Roller cam 185 is seen to have cam roller 188 which is rotatably mounted to shaft 186. Extending from the back 163 of the mounting bracket 160 is the slider fin 165 which is engaged by retention plate 175 having sliding groove 176 therein for receiving fin 164. Retention plate 175 is mounted to leg 171.

Referring now to FIG. 5, the apparatus 10 is seen to have drive motor 15 connected to transmission 16 which connects to shaft 17. Shaft 17 causes the table 110 to rotate between the nests 140 to the various work stations in succession. Motor 200 is an indexing motor which precisely rotates the nest members 140 to the various work stations. Also seen in FIG. 5 is the conventional frame 120 for supporting a conventional rotary vacuum system 125 which provides vacuum to nest members 140.

The initial work station 200 is illustrated in FIG. 1 and FIG. 6. Work station 200 is seen to receive covers 700 from track 50. The "pick and place" unit 210 is located at work station 200 and is seen to have lower 219 mounted to base 65 and upper frame 215. Pick and place unit 210 is a conventional, commercially available unit or equivalent thereof, e.g., an ATS Pick and Place Unit, manufactured by ATS, Inc., Burlington, Ontario, Canada. Slidably mounted to frame 215 is the pick and place head unit 220. Pick and place head unit 220 is mounted to rods 216 which slide in frame 215 when pneumatic or hydraulic cylinder 230 is actuated. The cylinders useful to actuate the various components of the apparatus 10 may be pneumatic or hydraulic, preferably pneumatic or gas operated, and are referred to in this application as pneumatic/hydraulic. Pick and place head unit 220 is seen to have jaw unit 217 which is rotatably mounted to frame member 216 such that the pick and place head unit 220 is capable of 90° of rotation from track 50 to a nest member 140. The pick and place head unit 210 is seen to have in jaw unit 217 having the slidably mounted opposed jaw members 225 for engaging covers 700. The pick and place head unit 220 can be moved toward and away from the nest 140 by the cylinder actuator 230. The jaw members 225 are seen in FIG. 8 and are actuated by an internal pneumatic/hydraulic cylinder (not shown). Jaw members 225 are seen to have projections 226. The pick and place head unit 220 is capable of up and down motion. The vertical movement of head unit 220 is controlled by pneumatic/hydraulic cylinders 218 mounted to frame 215 and lower frame 219. A nest 140 at work station 200 is engaged by a cam bracket 340 in order to align the nest 140 precisely with the pick and place unit 200.

Work station 270 is seen to be mounted to the top 101 of base 100. Referring now to FIGS. 9, 10, 11, and 12, the work station 270 is seen to have clip feeding member 280 which receives clips 2 from track member 30. Clip feeding member 280 is seen to have grooves 282 for receiving the legs of the ligating clips 2 and centrally extending Section 285 which has a configuration which generally conforms to the configuration of the ligating clips 2. Mounted to either side of the member 280 and partially covering the grooves 282 are the retention plate members 288 which prevent the ligating clips 2 from escaping from the member 280. The station 270 is seen to have support frame 290 mounted to the top 101 of frame 100. The support bracket 300 is seen to be mounted to the support frame 290. Mounted to the top leg 292 of support bracket 290 is the receiving plate 300. Receiving plate 300 has top surface 302 for slidably receiving slider plate 310. Slider plate 310 is seen to have ligating clip receiving groove 312 for receiving ligating clips 2 and transferring ligating clips 2 by sliding over the top surface 302 of plate 300 and thereby moving a clip 2 into a cavity of a cover 700 and a comb 145 maintained in the nest 140. Plate 300 is seen to have retaining vacuum ports 314 for retaining clips 2 in groove 312. The slider plate 310 is actuated by actuating pneumatic/hydraulic cylinder 320 mounted to the frame 290. The nest 140 is displaced vertically at station 270 so that the slider plate 310 can insert a clip 2 in each cavity of the cover 700. Mounted to the top surface 101 at station 270 is the indexing base bracket 360 having vertical leg 361 and horizontal leg 362. Extending from the front side of leg 361 is the fin member 365. Cam bracket 340 is seen to be a U-shaped member having horizontal legs 341 and web 342. Legs 341 have inner cam surfaces 345. The bottom leg of cam bracket 340 is mounted to bracket 350 having top leg 351 and bottom leg 352. Extending from the back side of leg 352 is the fin engagement channel 356 for engaging fin 362. Extending from the back of web 342 is the bracket member 380. Mounted to member 380 is the indexing nut 382. Mounted to the top 101 of frame 100 is the indexing motor 370 having shaft 371 coupled to indexing screw 375 which engages indexing nut 382.

Optional work station 900 is seen in FIG. 1. At optional work station 900, a conventional computer vision system 910 inspects the covers 700 to determine whether or not the covers 700 have a clip in each cavity 710. Covers which do not have a complete load of clips 2 are identified and are removed to a reject bin at work station 500.

Figure 14:
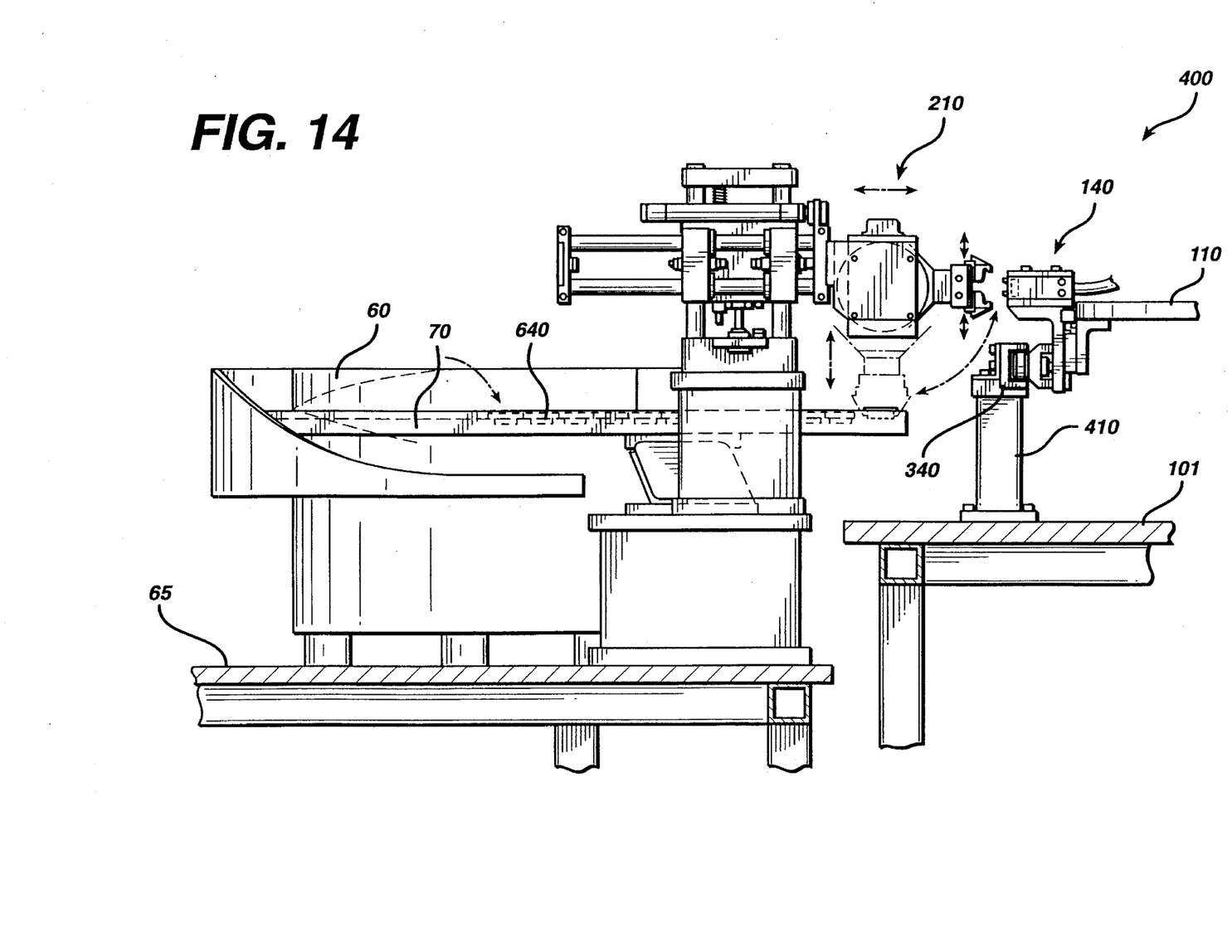
FIG. 14 is a side view of a cartridge pick and place transfer mechanism showing the transfer of a cartridge into a nest.

Work station 400 is seen FIG. 1 and FIG. 14. Work station 400 is seen to receive covers bases 640 from track 70. A pick and place unit 210 as described above is located at work station 400. Pick and place head unit 210 moves bases 640 from track 70 to nest 140 and engages the base 640 with the cover 700 to form assembled cartridge 690 containing clips 2. Mounted to the top 101 of frame 100 at station 400 is the cam support member 410. Mounted to the top of support member 410 is a cam bracket 340 for engaging a cam engagement roller wheel 188.

Figure 15:
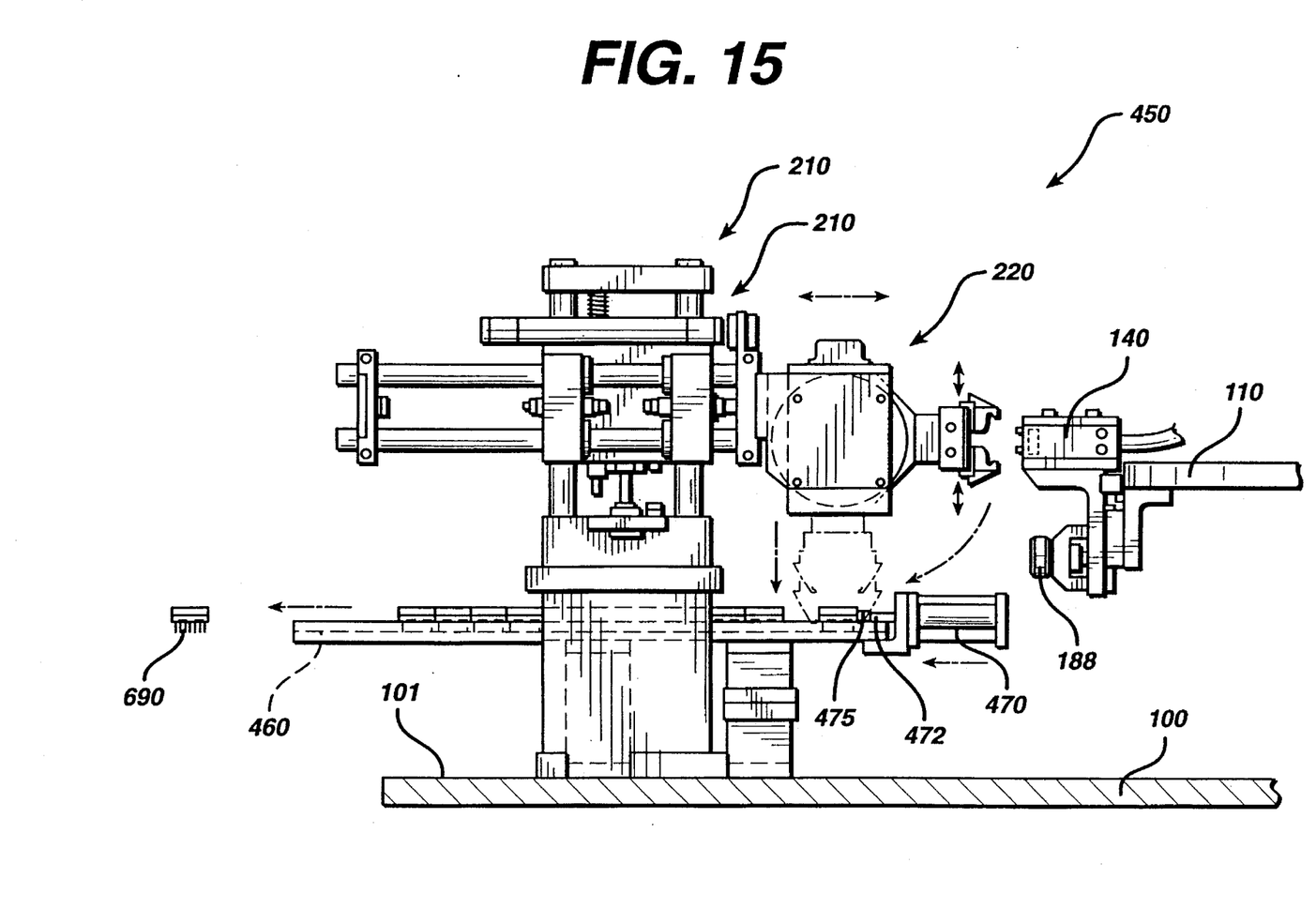
FIG. 15 is a side view of a loaded cartridge pick and place transfer mechanism illustrating the transfer of loaded cartridges onto a vibrating track.

Located at work station 450 as seen in FIGS. 1 and 15 is a pick and place unit 210 for removing loaded cartridges 690 from nests 140. The loaded cartridges 690 are placed onto track 460 which moves them to a suitable package or container for transportation to a storage or quarantine area. Cartridges 690 are moved by pneumatics hydraulic cylinder 470 having rod 472 and bullet nose 475. Cylinder 470 is mounted to the end of track 460. Also seen in FIG. 1 is optional reject station 500. Station 500 has a ramp 525 for receiving rejected cartridges 690 as identified by vision system 910. Any cartridges 690 having low clip loads are released form the cavities of the nests 140 by releasing the vacuum to the plenum cavity 142 of the nests 140 and allowing the cartridge 690 to then eject or fall to the ramp 525 and the bin 530.

The apparatus 10 of the present invention operates in the following manner.

Starting with work station 200, as seen in FIG. 6, the rotary index table 110 rotates such that a nest member 140 is aligned with a pick and place unit 210 located at work station 200 by cam bracket 340 which engages roller cam 188. Covers 700 contained in vibrating bowl 40 are moved up ramp 42 to track 50. The pick and place head unit 220 rotates 90° and is actuated downwardly so that the jaw unit 217 engages a cover 700. Next, the head unit 220 rotates 90° and the head unit 220 is displaced upwardly by pneumatic/hydraulic cylinders 218. Next, the head unit 220 is displaced toward nest 140 by the cylinder actuator 230. This causes cover 700 to move through opening 143 and to be engaged in the cavity 142 of the nest member 140 such that the teeth 147 of the comb members 145 are contained within cavities 710 of cartridge cover 700 and the cover 700 is engaged by the comb member 145.

Next, the rotary index table 110 is rotated to work station 270 where ligating clips 2 are inserted into the cavities 710 of the cover 700 and teeth 147 of comb members 145. Ligating clips 2 are contained in vibrating bowl 20 and are moved up ramp 22 to the clip feeding member 280. The slider plate 310 engages a ligating clip 2 and transfers the ligating clip over the top surface 302 of plate 300 into a cavity 710 of cover 700 in the nest 140. The slider plate 310 is actuated by the actuating cylinder 320. The nest 140 is indexed with respect to the slider plate such that the nest and the cover 700 are moved vertically as each cavity 710 is filled with a ligating clip 2 so that all of the cavities 710 of the cover 700 may be filled with ligating clips.

Next, after the cover 700 has been filled with ligating clips 2, each nest 140 containing a cover 700 filled with clips 2 is rotated first to an optional vision inspection station 900 where an optical vision apparatus 910 inspects the cavities 710 of the cover 700 to determine whether each cavity 710 has received a clip 2. Those covers which are short on clip count are identified.

Then the nest 140 is rotated to station 400 where bases 640 are loaded by a pick and place mechanism 210 into the cavity 142 and into cover 700, thereby forming the assembled clip cartridge 690 containing ligating clips 2. The nests 140 are again positioned at this work station by a cam bracket 340. At work station 400 bases 640 are contained in a vibrating bowl 60. The bases 640 are vibrated along ramp 62 to track 70. A pick and place unit 210 picks the bases from track 70 and inserts them into the loaded cover 700 contained in the nest 140 in a similar manner as that described for station 200.

Next, the assembled cartridge 690 in the nest 140 is indexed to station 450. At station 450, a pick and place unit 210, operating in a similar manner to the pick and place units 210 at stations 400 and 200, removes the assembled cartridge 690 from the nest 140 and places it onto the track 460. Cylinder 460 having rod 462 and bullet shaped nose 465 pushes the cartridges 690 along track 460. Finally, if desired, an optional rejection station 500 may be included and each nest 140 is indexed in turn to station 500. Any cartridges containing less than the required count of clips 2 are ejected or fall from the nests 140 by releasing vacuum to the plenum cavity 142 of the nest 140 and allowing the cartridges 690 to fall out from the nest 140 onto ramp 525 and into reject bin 530. Optional inspection station 500 may contain, if desired, a conventional vision (computer-controlled) inspection system which will control an optional conventional pick and place unit 210 which will remove any cartridges 690.

The novel process and apparatus of the present invention have many advantages. It is now possible to automatically load ligating clips into ligating clip cartridges in a highly automated, fast and accurate manner. The machinery is easy to use since clips, cartridge bases, and cartridge covers are simply dumped in bulk into bins and then automatically fed to the apparatus 10 and assembled.

Although this invention has been shown and described with respect to detailed embodiments thereof, it will understood by those skilled in the art that various changes in form and detail thereof may be made without departing from the spirit and scope of the claimed invention.

We claim:

1. An apparatus for loading ligating clips into a ligating clip cartridge, wherein the cartridge comprises a cover having a plurality of separated cavities for receiving ligating clips and openings in the cover in communication with the cavities, and a base which fits into the cover, the apparatus comprising:

a base member having a top;

an index table member rotatably mounted to the top of the base member, said index table having a top, a bottom and an outer periphery means for rotating the index table member, said rotating means mounted to the base member at least one nest member mounted to the periphery of the index table member, said nest member having a cavity for receiving a ligating clip base member;

cam follower means mounted to each nest member for raising and lowering the nest member with respect to the index table member;

cam means mounted to the base adjacent to each work station for engaging the cam follower means a first work station located proximately to the index table, said work station comprising means for feeding a cover in the cavity of each nest member;

a second work station located proximately to the index table, said second work station comprising means for feeding at least one ligating clip into cavities contained in a clip cover mounted in the cavity of a nest member;

a third work station located proximately to the index table, said third work station comprising means for inserting a base into a clip cover containing at least one ligating clip mounted in the cavity;

a fourth work station located proximately to the index table, said fourth Work station comprising means for removing an assembled ligating clip cartridge from the cavity of each nest member; and means for indexing the index table member so that each nest member is successively moved to each work station.

2. The apparatus of claim 1 further comprising a fifth work station located proximately to the index table, said fifth work station comprising means for visually inspecting the cavity of each nest member.

3. The apparatus of claim 1 wherein the nest member additionally comprises a comb member mounted in the cavity.

4. The apparatus of claim 1, further comprising means for raising and lowering each nest adjacent to each work station.

5. The apparatus of claim 4 wherein the means for lowing and raising the nest members comprises a cam follower mounted to the index table and a cam mounted to the top of the base member adjacent to each work station.

6. The apparatus of claim 1 further comprising means for feeding covers to the first work station.

7. The apparatus of claim 6 wherein the means for feeding covers comprises a vibratory bowl and a vibrating track.

8. The apparatus of claim 1 additionally comprising means for feeding the clips into the second work station.

9. The apparatus of claim 8 wherein the means for feeding the clips comprises a vibratory bowl and a vibrating track.

10. The apparatus of claim 1 additionally comprising means for feeding bases to the third work station.

11. The apparatus of claim 10 wherein the means for feeding bases comprises a vibrating bowl and a vibrating track.

12. The apparatus of claim 1 wherein the second work station comprises pick and place unit mounted to a base, said pick and place unit comprising;

a rotatable head mounted to a frame;

a pair of opposed jaws mounted to said head, said jaws movable with respect to each other;

means for rotating the head mounted to the frame;

means for moving the head up and down mounted to the frame; and means for moving the head toward and away from the index table mounted to the frame.

13. The apparatus of claim 1 wherein the second work station comprises;

a slider base having a top;

a slider plate mounted to the top of the slider base, said slider plate having a top surface, a slider bar, slidably engaged on the top surface of the slider plate, said slider bar having a groove for engaging a ligating clip;

means for sliding the slider bar toward and away from the table such that the groove enters into the cavity of a nest member.

14. The apparatus of claim 1 where vacuum means are mounted to each nest in communication with each cavity.

15. The apparatus of claim 1 wherein the insertion means for the third work station comprises a pick and place unit comprising;

a rotatable head mounted to a frame;

a pair of opposed jaws mounted to said head, said jaws movable with respect to each other;

means for rotating the head mounted to the frame;

means for moving the head up and down mounted to the frame; and means for moving the head toward and away from the index table mounted to the frame.

16. The apparatus of claim 1 wherein the means for removing the assembled ligating clip cartridge at said fourth work station comprises a pick and place unit comprising; a rotatable head mounted to a frame;

a pair of opposed jaws mounted to said head, said jaws movable with respect to each other;

means for rotating the head mounted to the frame;

means for moving the head up and down mounted to the frame; and means for moving the head toward and away from the index table mounted to the frame.

17. The apparatus of claim 1, wherein the camming means adjacent to the second work station is mounted to an index screw such that the camming means can be moved up and down with respect to the index table.

18. A method for loading ligating clips into a ligating clip cartridge, wherein the cartridge comprises a cover having a plurality of separated cavities for receiving ligating clips and openings in the cover in communication with the cavities, and a base which fits into the cover, the apparatus comprising:

a base member having a top;

an index table member rotatably mounted to the top of the base member, said index table having a top, a bottom and an outer periphery means for rotating the index table member, said rotating means mounted to the base member at least one nest member mounted to the periphery of the index table member, said nest member having a cavity for receiving a ligating clip base member;

cam follower means mounted to each nest member for raising and lowering the nest member with respect to the index table member;

cam means mounted to the base adjacent to each work station for engaging the cam follower means a first work station located proximately to the index table, said work station comprising means for feeding a cover in the cavity of each nest member;

a second work station located proximately to the index table, said second work station comprising means for feeding at least one ligating clip into cavities contained in a clip cover mounted in the cavity of a nest member;

a third work station located proximately to the index table, said third work station comprising means for inserting a base into a clip cover containing at least one ligating clip mounted in the cavity;

a fourth work station located proximately to the index table, said fourth work station comprising means for removing an assembled ligating clip cartridge from the cavity of each nest member; and means for indexing the index table member so that each nest member is successively moved to each work station, said method comprising:

rotating the index table so that each nest successively moves to each work station:

loading a cartridge cover into each nest at the first station;

loading a plurality of ligating clips into the cavities of each cover at the second station;

loading a base into the loaded cover to form a loaded cartridge at the third work station; and, removing the loaded cartridge from each nest at the fourth work station.

19. The method of claim 18, additionally comprising the step of visually inspecting each cover after the ligating clips have been loaded at the second station to determine if each cavity contains a clip.

* * * * *